United States Patent
Kross et al.

(10) Patent No.: US 11,096,636 B2
(45) Date of Patent: Aug. 24, 2021

(54) METHOD AND APPARATUS TO OBTAIN LIMITED ANGLE TOMOGRAPHIC IMAGES FROM STATIONARY GAMMA CAMERAS

(71) Applicant: JEFFERSON SCIENCE ASSOCIATES, LLC, Newport News, VA (US)

(72) Inventors: Brian Kross, Yorktown, VA (US); Andrew Weisenberger, Yorktown, VA (US); Ben Welch, Hampton, VA (US); David Gilland, Gainesville, FL (US); Seung Joon Lee, Poquoson, VA (US)

(73) Assignee: JEFFERSON SCIENCE ASSOCIATES, LLC, Newport News, VA (US)

( * ) Notice: Subject to any disclaimer, the term of this patent is extended or adjusted under 35 U.S.C. 154(b) by 12 days.

(21) Appl. No.: 16/448,911

(22) Filed: Jun. 21, 2019

(65) Prior Publication Data

US 2019/0388041 A1    Dec. 26, 2019

Related U.S. Application Data

(60) Provisional application No. 62/688,133, filed on Jun. 21, 2018.

(51) Int. Cl.
*A61B 6/12* (2006.01)
*A61B 6/00* (2006.01)
*A61B 6/06* (2006.01)

(52) U.S. Cl.
CPC ................ *A61B 6/12* (2013.01); *A61B 6/06* (2013.01); *A61B 6/4258* (2013.01); *A61B 6/502* (2013.01)

(58) Field of Classification Search
CPC .......... A61B 6/12; A61B 6/06; A61B 6/4258; A61B 6/502
See application file for complete search history.

(56) References Cited

U.S. PATENT DOCUMENTS

| | | | | |
|---|---|---|---|---|
| 4,419,585 | A * | 12/1983 | Strauss | G21K 1/025 250/363.1 |
| 5,436,958 | A * | 7/1995 | Taylor | G21K 1/04 250/363.1 |
| 5,519,221 | A * | 5/1996 | Weinberg | A61B 6/0414 250/363.02 |
| 6,377,838 | B1 * | 4/2002 | Iwanczyk | A61B 6/0414 250/363.02 |
| RE43,499 | E | 7/2012 | Kieper et al. | |
| 2001/0056234 | A1 * | 12/2001 | Weinberg | A61B 6/4258 600/436 |
| 2010/0260316 | A1 * | 10/2010 | Stein | A61B 6/5235 378/37 |
| 2010/0261997 | A1 * | 10/2010 | Ren | A61B 6/4411 600/424 |

(Continued)

*Primary Examiner* — Blake C Riddick

(57) ABSTRACT

A nuclear imaging system and method for performing three-dimensional imaging of anatomical structures. The system and method includes two or more gamma ray detectors each used in combination with a variable-slant hole collimator. The detectors are positioned in close proximity to, or in contact with, the structure being imaged. The detectors remain in a stationary position during the data collection process. An imaging or reconstruction method is then used to reconstruct a three-dimensional image from the data derived from the detectors.

2 Claims, 3 Drawing Sheets

(56) References Cited

U.S. PATENT DOCUMENTS

| | | | |
|---|---|---|---|
| 2010/0329418 A1* | 12/2010 | Blevis | A61B 6/502 378/37 |
| 2012/0250969 A1* | 10/2012 | Stein | A61B 6/4291 382/131 |
| 2013/0158389 A1* | 6/2013 | O'Connor | A61B 8/4416 600/424 |
| 2016/0296186 A1* | 10/2016 | Hugg | A61B 6/12 |
| 2017/0040077 A1* | 2/2017 | Lee | G21K 1/04 |

\* cited by examiner

2(a)

2(c)

2(b)

2(d)

METHOD AND APPARATUS TO OBTAIN LIMITED ANGLE TOMOGRAPHIC IMAGES FROM STATIONARY GAMMA CAMERAS

The United States Government may have certain rights to this invention under Management and Operating Contract No. DE-AC05-06OR23177 from the Department of Energy.

FIELD OF THE INVENTION

The present invention relates to nuclear imaging methods and techniques, and, more specifically, a device and method for use in functional imaging and for improved cancer detection.

BACKGROUND OF THE INVENTION

Breast cancer is one of the leading causes of death for women in the United States. It is estimated that approximately 1 in 8 women born in the U.S. today will develop breast cancer during their lifetimes. As with all cancers, early detection is critical for improved survival probability. X-ray mammography is considered the best method to detect breast cancer at early stages; however, this imaging method has a high false negative rate for patients with radio-dense breast tissues and a relatively low positive predictive value. Mammography, however, is structural imaging only and requires painful clamping in order to get the breast to approximate a uniform thickness. Further, mammography provides poor sensitivity for women with dense breasts.

Various alternative methods are utilized for cancer, including breast cancer, imaging, including contrast-enhanced MRI, optical imaging, dedicated CT, and positron emission tomography. Nuclear medical imaging, in particular, is a critical tool in the diagnosis and treatment of many diseases and conditions, including breast cancer, where it has historically been referred to as scintimammography. All of these methods, however, possess certain limitations. For instance, positron emission tomography requires a ring or partial ring around a structure so the detector array cannot be in close proximity to a target and, further, there can be a significant cost for such a device. Conventional three-dimensional nuclear medicine imaging, SPECT, however, requires a camera that orbits around a target so, just as with PET, the detector cannot be in close proximity to that target.

One of the most promising methods serving a complementary role to mammography, particularly for women with radio-dense breasts, is scintimammography, more recently known as molecular breast imaging. It has been established that molecular breast imaging can complement mammography in women with dense breasts. Indeed, multi-modal imaging, with molecular breast imaging and mammography, is a highly effective imaging method.

In general terms, molecular breast imaging relies upon a basic detector device, such as a gamma camera, used to detect radiation emitted from radioisotopes for planar imaging. A typical clinical gamma camera is 50 cm in diameter, whereas a molecular breast imaging camera is 15 cm by 25 cm. For certain medical imaging diagnostic procedures, such as cardiac and thyroid studies, a single gamma camera is employed to obtain planar images. In these cases the patient is injected with a radioactive compound called a radiopharmaceutical which will accumulate in a particular tissue type, e.g., cancerous tissue. The radioisotope decays and emits a high energy photon which is detectable outside the patient through the use of a gamma camera.

In most tomographic imaging applications in the current art, a gamma camera is rotated completely around the patient to get multiple views (typically about sixty in number) to obtain a three-dimensional image of the bio-distribution of the radiopharmaceutical. Situations frequently arise in which it is not possible to obtain a complete orbit about the patient. In addition, allowing the camera to remain stationary, i.e., in place for the duration of data collection, and in close proximity to the patient can provide for more accurate reconstruction and imaging.

It is therefore preferable to have a device and method that overcomes the foregoing difficulties and allows for more complete three-dimensional imaging, particularly breast imaging, with superior clarity and resolution, in situations where detector orbit is restricted or one desires to benefit from the advantages of stationary detector(s). It is further preferable to reduce the overall amount of radiation necessary to accomplish the desired imaging so as to reduce the radiation dose for the persons having the imaging process performed upon them.

OBJECT OF THE INVENTION

It is an object of the invention to provide a gamma camera system and a method of functional imaging which improves spatial resolution in the imaging process while facilitating the near-complete three-dimensional acquisition of a desired target image, without moving the detector from the structure being imaged.

SUMMARY OF THE INVENTION

The invention is an imaging system and method used to perform three-dimensional functional imaging of anatomical structures, such as breasts, for the purpose of locating, identifying, and evaluating cancerous lesions and similar pathologies. The system is composed of two or more gamma ray detectors each of which incorporates a variable-angle slant hole collimator. The detectors are positioned in close proximity to the anatomical structure of interest, and, in fact, may be, and remain, in contact with the structure during the entire imaging process. A limited-angle tomosynthesis reconstruction algorithm is then used to reconstruct a three-dimensional image from the data derived from the detectors.

BRIEF DESCRIPTION OF THE DRAWINGS

Reference is made herein to the accompanying drawings, which are not necessarily drawn to scale, wherein.

DETAILED DESCRIPTION

The present invention is a multi-headed high sensitivity and high spatial resolution dynamic imaging system and method. The imaging system includes two or more gamma ray detectors, each equipped with a variable angle slant hole ("VASH") collimator. The VASH collimators allow each gamma camera to collect projection image data over a continuous angular range of acceptance angles. The detectors remain stationary during the imaging process. The only thing that changes is the aperture angles of the VASH collimators. An image is then reconstructed from the combined data from the detectors.

More specifically, the system is composed of at least two gamma detectors, also referred to as gamma cameras. Each gamma camera incorporates a variable-angle, slant hole ("VASH") collimator. The VASH collimator consists of a stack of thin plates, composed of tungsten or an analogous material, that contain a matrix of holes created by photoetching. When the holes of the plates align, a parallel hole collimator is created. By shearing the stack of plates to varying degrees, a variable angle slant hole collimator is created. The VASH collimator design is particularly suitable for imaging a breast under mild compression. The detector can remain stationary and flush against the breast or a compression paddle to minimize object distance for best spatial resolution/sensitivity trade-off compared with conventional detectors.

Figure 1:
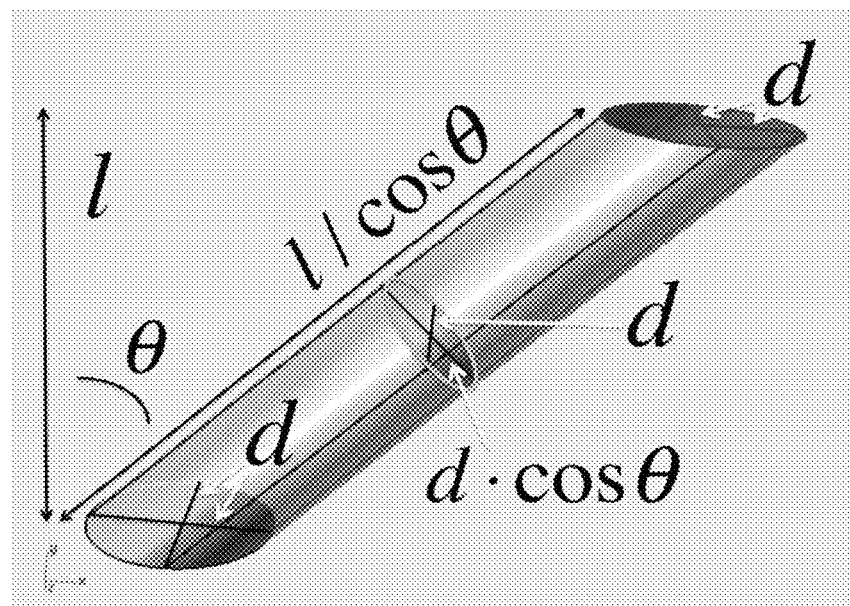
FIG. 1 is a perspective view of a single channel found in a variable-angle slant hole collimator.
Figure 2:
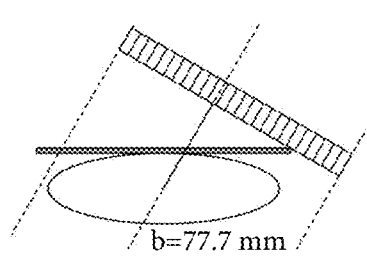
FIG. 2 illustrates a conventional parallel hole collimator compared to a variable-angle slant hole collimator.
Figure 2:
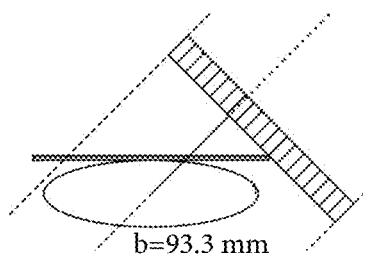
Figure 2:
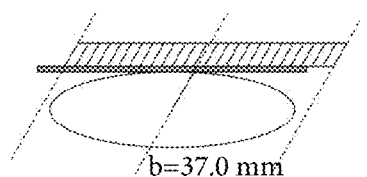
Figure 2:
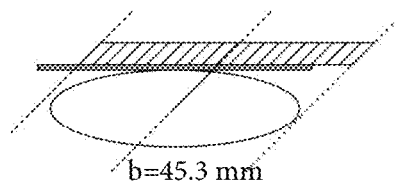

Changes in the VASH collimator hole geometry with slant angle impart unique properties in terms of the spatial resolution and sensitivity compared to static slant hole or converging collimators. Referring to FIGS. 1 and 2, l is the thickness of the stack of plates—which is the collimator hole length with zero slant angle—and d is the diameter of the holes etched into the plates. As shown in FIG. 1, with slant angle θ, the effective hole length is l/cos θ. The hole cross-section perpendicular to the photon path (ellipse) becomes increasingly elliptical with θ: in the slant, or lateral, dimension the hole width is d cos θ, while the width in the orthogonal, anterior-posterior (AP) dimension remains d. Therefore, the collimator spatial resolution ($R_{coll}$), which is proportional to hole diameter divided by length is anisotropic for non-zero θ. Use of this geometry in the collimator significantly improves the signal to noise ratio of the imaging process as compared to planar, conventional SPECT with a parallel hole collimator.

The present invention is a multi-headed limited-angle tomography molecular breast imaging system relying upon the unique advantages of the VASH collimator. Each gamma ray detector is positioned in close proximity to an anatomical structure of interest, e.g., the breast. Depending on the number of detectors, the detectors' field-of-view has an angular separation of 180 degree (in the case of two opposing detectors), 90 degrees (two or more right angle detectors) or any other angle (for multiple-view detector array). The detectors serve a dual purpose. The primary purpose of each detector is to image the anatomical structure from various angles. However, due to their potential positioning in actual contact with the structure, the detectors may, under certain circumstances, also be used to immobilize the anatomical structure being imaged.

The VASH collimator is used to define the acceptance angle of each detector. As explained above, the VASH collimator provides an array of apertures for the gamma rays to reach the detector. The apertures can be defined by a grid of gamma ray attenuating material and further, can be at an angle normal to the surface of the detector. The collimator enables the detector to collect projection image data from a range of acceptance angles defined by the apertures and/or from a range of other angles defined by penetration of the gamma ray attenuating material.

The VASH collimator system allows scanning, and the creation of three dimensional images, while in extreme proximity to, or in contact with, the target structure, e.g., the breast. The detector does not need to move away from the breast in order to obtain this information and does not need to rotate about the object being imaged. The system can view a structure, such as a breast, from multiple angles without the need to remove the structure from an immobilizing device or the need to reposition either the structure or the gamma camera. Since the breast is not moved during the imaging process, the distribution of the breast does not change which improves the data obtained. If the camera is moved, the breast may move as well. Further, the close proximity of the detector to the imaged structure increases the position resolution of the imaging process.

Figure 3:
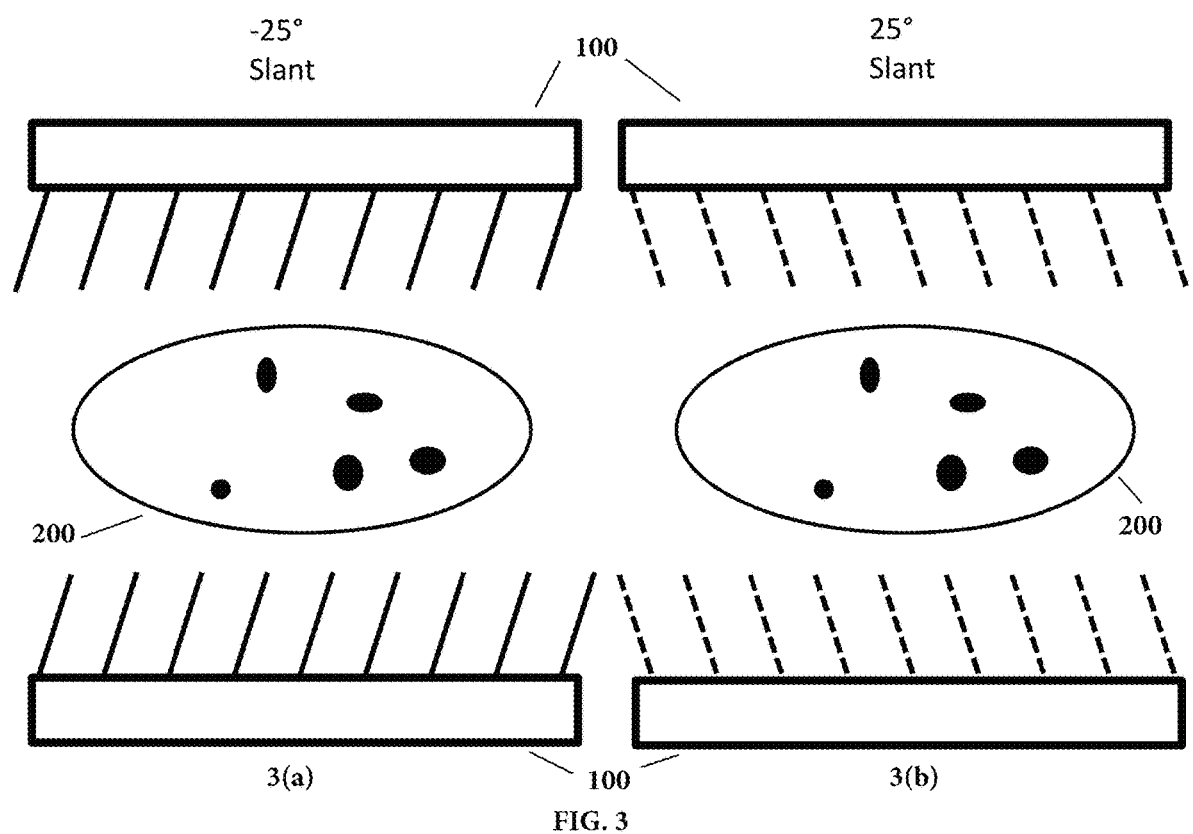
FIG. 3 illustrates the two-headed detector system positioned on opposite sides of a target structure.

The preferred embodiment is a dual-head VASH gamma camera system, as shown in FIG. 3, wherein the detectors 100 are positioned on opposing sides of the breast 200 and both detectors 100 acquire projection data over a 50 degree angular range. The collimators are designed to create slant angles from −25 deg. to +25 deg. While the preferred embodiment of this system would rely upon two gamma detectors, three, four, or even more such detectors could be used.

As noted above, the placement of the detectors directly against the breast significantly minimizes negative spatial resolution effects by minimizing the target to collimator distance. The number, geometry, and positioning of the gamma cameras can be adjusted in order to improve detection efficiency.

The imaging processing or reconstruction method would consider the following parameters: (i) the location of the various detectors, (ii) information about the field of view of the detectors, (iii) information about the field of view at each acceptance angle of the VASH collimator, (iv) information about the response of the detectors to gamma rays originating within the acceptance angle of the field of view of the VASH collimator, and (v) information about the response of the detectors to gamma rays originating outside the acceptance angle but within the field of view of the VASH collimator and penetrating the attenuating material. The reconstruction method is used to determine the spatial distribution of gamma ray emitting structures within that field of view of the apparatus.

The imaging system uses advanced image reconstruction methods to manipulate and process the acquired data. The system employs iterative methods, which have demonstrated superior performance to filtered back projection for the limited angle application of breast tomosynthesis and have been applied successfully for reconstructing limited angle SPECT data.

The method disclosed herein serves to improve tumor detectability over standard molecular breast imaging and, further, provides significantly more coordinate information, thereby helping localize the tumor with a much greater degree of specificity. The use of high speed mathematically computed image reconstruction algorithms to return image information while the patient is under compression also allows a clinician to perform a biopsy, or take other action, while the tissue is still under compression or immediately after imaging.

By having two VASH collimator enabled detectors appropriately positioned, one can obtain nearly full tomography of the breast and, consequently, more complete three-dimensional imaging. Further, this system allows for the detection of smaller lesions because of the proximity of the detectors to the patient and the resulting higher spatial resolution.

It will also be noted that the improved image quality of the system may permit a reduction in radiation dose required for a satisfactory image. The following results are easily achievable using a two-headed detector system: a 7.8 mm lesion was detectable at quarter dose (5 mCi injected dose vs a standard dose of 20 mCi), a 6.2 mm lesion was detectable at half dose (10 mCi), and a 4.9 mm lesion was detectable at full dose (20 mCi).

While the invention has been described in reference to certain preferred embodiments, it will be readily apparent to one of ordinary skill in the art that certain modifications or variations may be made to the system without departing from the scope of invention claimed below and described in the foregoing specification.

What is claimed is:

1. A method of imaging an anatomical structure comprising the steps of: administering a gamma radiation emitting radiopharmaceutical such that at least a portion of said radiopharmaceutical accumulates in an anatomical structure being imaged; positioning at least two gamma ray detectors, each incorporating a variable-angle slant hole collimator, such that each detector has the structure in its respective field of view; defining one or more acceptance angles for each gamma ray detector; acquiring projection image data from the structure over a continuous angular range of the acceptance angle of each gamma ray detector; and, generating a gamma ray image of the anatomical structure by evaluating and considering the data derived from the imaging method, said data comprising the location of the detectors, the field of view of the detectors, the response of the detectors to gamma rays originating within the acceptance angle of the collimator and the response of the detectors to gamma rays originating within the field of view but outside the acceptance angle of the collimators.

2. The method of claim 1 wherein generating a gamma ray image further comprises iteratively processing said data to obtain limited angle SPECT images of the accumulated radiopharmaceuticals in said structure.

* * * * *